US009278367B2

(12) United States Patent
Cooper

(10) Patent No.: US 9,278,367 B2
(45) Date of Patent: Mar. 8, 2016

(54) PRECISION PUMPING SYSTEM FOR SPRAY TREATMENT CYCLES

(71) Applicant: SUNLESS, INC., Macedonia, OH (US)

(72) Inventor: Steven C. Cooper, Athens, GA (US)

(73) Assignee: Sunless, Inc., Macedonia, OH (US)

( * ) Notice: Subject to any disclaimer, the term of this patent is extended or adjusted under 35 U.S.C. 154(b) by 239 days.

(21) Appl. No.: 14/029,413

(22) Filed: Sep. 17, 2013

(65) Prior Publication Data

US 2014/0076992 A1 Mar. 20, 2014

Related U.S. Application Data

(60) Provisional application No. 61/702,185, filed on Sep. 17, 2012.

(51) Int. Cl.
*B05B 15/12* (2006.01)
*B05B 12/00* (2006.01)
(Continued)

(52) U.S. Cl.
CPC .............. *B05B 12/004* (2013.01); *A61M 35/00* (2013.01); *B05B 9/0413* (2013.01); *B05B 9/0423* (2013.01); *B05B 12/08* (2013.01); *B05B 12/10* (2013.01); *B05B 12/122* (2013.01); *F04B 9/025* (2013.01); *F04B 13/00* (2013.01);
(Continued)

(58) Field of Classification Search
CPC ...... F04B 17/03; B05B 15/12; B05B 13/0405
USPC ........ 239/73, 67, 68, 69; 604/19, 23, 24, 289, 604/290; 607/81, 82; 118/33
See application file for complete search history.

(56) References Cited

U.S. PATENT DOCUMENTS

| 1,586,009 A | 5/1926 | Shelburne |
| 1,982,509 A | 11/1934 | Frank |

(Continued)

FOREIGN PATENT DOCUMENTS

| DE | 3540990 A1 | 5/1987 |
| DE | 3720938 A1 | 1/1989 |

(Continued)

OTHER PUBLICATIONS

European Search Report issued Mar. 19, 2015 in European Patent Application No. 13 18 4687.
(Continued)

*Primary Examiner* — Justin Jonaitis
(74) *Attorney, Agent, or Firm* — Venable LLP; Steven J. Schwarz; Frank M. Gasparo

(57) ABSTRACT

Embodiments disclosed herein propose a precision spray pumping system including a positive displacement pump in fluid communication with at least one spray nozzle. The positive displacement pump includes a displaceable member, and displacement of the displaceable member corresponds to a pumping cycle of the positive displacement pump. A controller is in communication with the positive displacement pump. The controller is operable to apply an actuation parameter to direct a displacement of the displaceable member and is also operable to receive an indication of an actual position of the displaceable member. The controller is further operable to compare a predetermined actuation parameter associated with an expected displacement of the displaceable member to a measured actuation parameter associated with the actual position of the displaceable member.

18 Claims, 7 Drawing Sheets

(51) Int. Cl.

| | | |
|---|---|---|
| *A61M 35/00* | (2006.01) | |
| *B05B 9/04* | (2006.01) | |
| *B05B 12/08* | (2006.01) | |
| *B05B 12/10* | (2006.01) | |
| *B05B 12/12* | (2006.01) | |
| *F04B 9/02* | (2006.01) | |
| *F04B 13/00* | (2006.01) | |
| *F04B 17/03* | (2006.01) | |
| *B05B 13/04* | (2006.01) | |

(52) U.S. Cl.
CPC ............ *F04B 17/03* (2013.01); *B05B 13/0405* (2013.01); *B05B 15/12* (2013.01)

(56) References Cited

U.S. PATENT DOCUMENTS

| | | | |
|---|---|---|---|
| 2,139,133 A | 12/1938 | Paasche | |
| 2,267,264 A | 12/1941 | Bland | |
| 2,284,235 A | 5/1942 | Ronzi | |
| 2,401,504 A | 6/1946 | Paasche | |
| 3,007,178 A | 11/1961 | Altman et al. | |
| 3,057,558 A | 10/1962 | Verba et al. | |
| 3,344,992 A | 10/1967 | Norris | |
| 3,437,791 A | 4/1969 | Gardner | |
| 3,587,118 A | 6/1971 | Compton | |
| 3,596,834 A | 8/1971 | Cushing | |
| 3,662,407 A | 5/1972 | Colucci | |
| 3,721,250 A | 3/1973 | Walter et al. | |
| 3,759,449 A | 9/1973 | Ruthman et al. | |
| 3,770,201 A | 11/1973 | Sanders | |
| 3,780,943 A | 12/1973 | Lilja | |
| 3,854,489 A | 12/1974 | Doyle et al. | |
| 3,905,379 A | 9/1975 | Churas et al. | |
| 3,947,659 A | 3/1976 | Ono | |
| 3,989,143 A | 11/1976 | Broussard | |
| 4,056,078 A | 11/1977 | Blafford et al. | |
| 4,114,022 A | 9/1978 | Braulke, III | |
| 4,130,120 A | 12/1978 | Kohler, Jr. | |
| 4,149,536 A | 4/1979 | Villard | |
| 4,166,473 A | 9/1979 | Bauer et al. | |
| 4,300,556 A | 11/1981 | Ochi et al. | |
| 4,382,424 A | 5/1983 | Altissimo | |
| 4,386,739 A | 6/1983 | Kwok | |
| 4,394,967 A | 7/1983 | Amiaut | |
| 4,485,503 A | 12/1984 | Rolando et al. | |
| 4,505,229 A | 3/1985 | Altissimo | |
| 4,523,080 A | 6/1985 | Bolton | |
| 4,597,757 A | 7/1986 | Ruderian | |
| 4,605,019 A | 8/1986 | Reynolds et al. | |
| 4,714,462 A * | 12/1987 | DiDomenico | 604/67 |
| 4,761,837 A | 8/1988 | Takeda | |
| 4,836,137 A | 6/1989 | Heine et al. | |
| 4,862,754 A * | 9/1989 | Nimberger | 73/864.62 |
| 4,901,379 A | 2/1990 | Chalberg et al. | |
| 4,915,303 A | 4/1990 | Hufgard | |
| 4,941,808 A * | 7/1990 | Qureshi et al. | 417/415 |
| 5,038,769 A | 8/1991 | Krauser | |
| 5,074,322 A | 12/1991 | Jaw | |
| 5,078,322 A | 1/1992 | Torntore | |
| 5,102,051 A | 4/1992 | Smith et al. | |
| 5,136,735 A | 8/1992 | Zimmerman | |
| 5,199,644 A | 4/1993 | Haferkorn | |
| 5,228,150 A | 7/1993 | Parker | |
| 5,241,974 A | 9/1993 | Tsai | |
| 5,261,427 A | 11/1993 | Dolev | |
| 5,339,540 A | 8/1994 | Edwards | |
| 5,387,200 A | 2/1995 | Kronstadt | |
| 5,520,519 A | 5/1996 | Birkeland | |
| 5,558,276 A | 9/1996 | Barrett et al. | |
| 5,603,341 A | 2/1997 | Johnson | |
| 5,642,570 A | 7/1997 | Lee | |
| 5,664,593 A | 9/1997 | McClain | |
| 5,738,728 A * | 4/1998 | Tisone | 118/638 |
| 5,864,894 A | 2/1999 | Fedele | |
| 5,971,298 A | 10/1999 | Millan et al. | |
| 5,991,937 A | 11/1999 | Safara | |
| 6,106,547 A | 8/2000 | Huei-Jung | |
| 6,117,915 A | 9/2000 | Pereira et al. | |
| 6,302,122 B1 | 10/2001 | Parker et al. | |
| 6,387,081 B1 | 5/2002 | Cooper | |
| 6,416,747 B1 | 7/2002 | Laughlin | |
| 6,418,573 B1 | 7/2002 | Masuda | |
| 6,554,208 B1 | 4/2003 | Venuto, Sr. | |
| 6,673,097 B1 | 1/2004 | Venuto, Sr. | |
| 6,802,830 B1 | 10/2004 | Waters et al. | |
| 6,923,794 B2 | 8/2005 | Ohmura | |
| 6,973,679 B1 | 12/2005 | Schad | |
| 7,004,407 B2 * | 2/2006 | Cooper | 239/550 |
| 7,041,089 B2 | 5/2006 | Laughlin | |
| 7,132,010 B2 | 11/2006 | Carlsson | |
| 7,297,211 B2 | 11/2007 | Cooper et al. | |
| 7,387,684 B2 | 6/2008 | Cooper et al. | |
| 7,462,242 B2 | 12/2008 | Cooper et al. | |
| 7,569,037 B1 | 8/2009 | Spivak | |
| 7,772,526 B2 | 8/2010 | Chuong | |
| 2002/0000237 A1 | 1/2002 | Laughlin | |
| 2003/0029488 A1 | 2/2003 | Baird | |
| 2003/0094510 A1 | 5/2003 | Laughlin | |
| 2003/0127542 A1 | 7/2003 | Cooper | |
| 2004/0147884 A1 | 7/2004 | Szurko | |
| 2004/0156793 A1 | 8/2004 | Golden et al. | |
| 2004/0228810 A1 | 11/2004 | Hamson et al. | |
| 2005/0059910 A1 | 3/2005 | Licht et al. | |
| 2005/0150467 A1 | 7/2005 | Jobal | |
| 2005/0242207 A1 | 11/2005 | Tejeda | |
| 2005/0279865 A1 | 12/2005 | Thomason et al. | |
| 2005/0281957 A1 | 12/2005 | Cooper et al. | |
| 2006/0032946 A1 | 2/2006 | Cooper et al. | |
| 2006/0064815 A1 | 3/2006 | Guerin et al. | |
| 2006/0102096 A1 | 5/2006 | Cho | |
| 2006/0118039 A1 | 6/2006 | Cooper | |
| 2006/0163382 A1 | 7/2006 | Spivak et al. | |
| 2006/0207013 A1 | 9/2006 | Deboer et al. | |
| 2006/0214027 A1 | 9/2006 | Micheli | |
| 2006/0231567 A1 | 10/2006 | Perrone | |
| 2006/0275555 A1 | 12/2006 | Colizza et al. | |
| 2006/0278661 A1 | 12/2006 | Cooper et al. | |
| 2007/0107121 A1 | 5/2007 | Smith et al. | |
| 2007/0169261 A1 | 7/2007 | Smith et al. | |
| 2007/0197982 A1 | 8/2007 | Thomason et al. | |
| 2007/0275021 A1 | 11/2007 | Lee et al. | |
| 2008/0071332 A1 | 3/2008 | Nelson et al. | |
| 2008/0237522 A1 | 10/2008 | Morris | |
| 2009/0114236 A1 | 5/2009 | Mehta | |
| 2009/0130044 A1 | 5/2009 | Choi et al. | |
| 2009/0272316 A1 | 11/2009 | Arnaud et al. | |
| 2009/0314857 A1 | 12/2009 | Thomason et al. | |
| 2010/0065655 A1 | 3/2010 | Hipperson | |
| 2010/0266776 A1 | 10/2010 | Cooper et al. | |
| 2011/0060195 A1 | 3/2011 | De Noray et al. | |
| 2011/0133001 A1 | 6/2011 | Cooper et al. | |
| 2011/0133004 A1 | 6/2011 | Thomason et al. | |
| 2011/0137268 A1 | 6/2011 | Thomason et al. | |
| 2011/0202019 A1 | 8/2011 | Cooper et al. | |
| 2011/0259974 A1 | 10/2011 | Cooper et al. | |
| 2013/0262033 A1 | 10/2013 | Henson | |

FOREIGN PATENT DOCUMENTS

| | | |
|---|---|---|
| EP | 0359943 A2 | 3/1990 |
| GB | 2139885 A | 11/1984 |
| GB | 2432785 A | 6/2007 |
| JP | 2000135111 A | 5/2000 |
| WO | WO-03/035325 A1 | 5/2003 |
| WO | WO-2004033107 A2 | 4/2004 |
| WO | WO-2004069322 A1 | 8/2004 |
| WO | WO-2004084983 A1 | 10/2004 |

(56) References Cited

FOREIGN PATENT DOCUMENTS

| | | |
|---|---|---|
| WO | WO-2010012903 A1 | 2/2010 |
| WO | WO-2010123922 A1 | 10/2010 |

OTHER PUBLICATIONS

Croda Material Safety Data Sheet, Croda Document #CRODA-PRO; SHE-51, Attachment A, Revision Date Dec. 9, 2005 (4 pages).

CRODAFOS CES Product Brochure, Croda Inc., Feb. 9, 2010 (9 pages).

CRODAFOS(tm) CES Data Sheet, "Targeted Delivery Agent for Skin Care," INCI Name*: Cetearyl Alcohol (and) Dicetyl Phosphate (and) Ceteth-10 Phosphate, PN-094R-1, Jan. 28, 2009 (10 pages).

CRODAFOS(tm) CS20A Data Sheet, Cetearyl Alcohol (and) Ceteth-20 Phosphate, "Primary Emulsifier for Pourable or Sprayable Emulsions," Apr. 14, 2010, DS-156R-7 (9 pages).

Tanning Essentials, Manual: Classic Tanning Essentials Spray Tan System, date unknown (8 pages).

VersaSpa(tm) age-defying sunless tanning and More: "HVLP Automatic Skin Treatment System, Owner's Manual Version 5.0," Sep. 2006 (42 pages).

\* cited by examiner

PRECISION PUMPING SYSTEM FOR SPRAY TREATMENT CYCLES

PRIORITY CLAIM

This application claims priority to U.S. Provisional Patent Application No. 61/702,185 filed on Sep. 17, 2012, and entitled Precision Pumping System for Spray Treatment Cycles, the disclosure of which is hereby incorporated by reference.

TECHNICAL FIELD

The present invention relates generally to skin treatment spray systems, and more particularly to a precision pumping system for the delivery of skin treatment solutions in multiple spray treatment cycles.

BACKGROUND

Booth spray systems for the application of skin lotions and cosmetics dispense a selectable variety of skin treatments including moisturizer and tanning treatments. Salon spray booths for spray tanning and skin treatments offer multiple spray sessions with selections from a wide variety of skin lotions and tanning products. Many of the booth systems have moving gantries that apply the spray evenly over the full body or can be user-programmed to apply only to the face or legs. Some booths are outfitted with booth pre-heaters and full body drying systems.

Automated booth spray systems used in salons consist basically of a booth structure that is either fully or partially enclosed with single or multiple spray nozzles positioned inside the booth. Reference is made to the following references generally directed to booth-type spray systems, the disclosures of which are hereby incorporated by reference: U.S. Pat. No. 6,199,557 to Laughlin filed on Apr. 19, 1999; U.S. Pat. No. 7,004,407 to Cooper filed on Dec. 4, 2002; U.S. Pat. No. 7,886,684 to Cooper et al. filed on Apr. 28, 2006; U.S. Pat. No. 8,201,288 to Thomason et al. filed on Aug. 24, 2009; U.S. Patent Application Publication No. 2010/0266776 by Cooper et al. filed on Apr. 20, 2010; and U.S. Patent Application Publication No. 2011/0133004 by Thomason et al. filed on Oct. 22, 2010.

The spray session is activated by the person receiving the spray treatment within the enclosure. An exhaust fan may be used to prevent overspray inside the booth or drifting spray escaping from the booth. Other booth features may include lights, voice prompts in different languages, heaters, skin drying systems, and interior washing and rinsing systems.

The electrical and mechanical components in the rinse, drain, spray, gantry, heat and exhaust systems of these automated spray booths are operated in a sequence during a spray session by a microprocessor based or other sequential controller with a manual input device such as a keypad or button panel. Spray session parameters such as liquid flow, duration of spray, heater temperature, and the like are set and adjusted by input to the controller. Salon personnel and/or consumers using the spray system may manually enter certain operation parameters for each spray session.

The spray solution used for spray tanning is generally a water-based mixture of DHA (dihydroxyacetone) and/or erythrulose and various other skin care ingredients such as aloe vera. Often a cosmetic bronzer is added along with pleasant scents and other ingredients to enhance the tanning results and experience, such as formulations to balance skin pH. For best results, the spraying of the solution utilizes a finely atomized spray (mist), as opposed to using a spray stream or large spray droplets, because the mist of solution provides even coverage and reduces the risk of streaking or running of the spray deposit.

The spray systems of these booth-type skin treatment sprayers generally include single or multiple containers or tanks containing liquid spray solution which is fed to the spray nozzles by single or multiple pumps or other methods, such as gravity or Venturi. Flow is generally controlled by solenoid valves and a mechanical pump for which flow rate can be varied by varying motor speed or pressure. Multiple nozzles may be stationary and positioned along the interior walls of the booth, or they may be mounted to a moving gantry. A spray system disclosed in U.S. Pat. No. 7,886,684 to Cooper et al., the disclosure of which is hereby incorporated by reference, utilizes a single dose cartridge tank system. This system is configured with a single nozzle that oscillates while moving on a gantry. In addition, sprayers can be operated without a mechanical pump, relying on gravity or Venturi feed to the nozzle.

Multiple batch tank systems on skin care booth sprayers allow approximately 30 to more than 100 sessions between changing or re-filling the tanks Booths with multiple tanks have the advantage of allowing a sequence of spray sessions with a choice of various lotions applied one after the other; for instance a moisturizer treatment may be applied after a tanning treatment, or a skin pH balancing spray may be applied before a tanning spray. Some booth models use refillable multiple tank systems with 2, 3 or 4 tanks. Many booth spray systems accommodate a more convenient bag-in-box system where multiple refillable and/or replaceable containers are received in a bay drawer of the unit as disclosed by U.S. Pat. No. 8,201,288 to Thomason et al. filed on Aug. 24, 2009, the disclosure of which is hereby incorporated by reference.

The liquid flow system of a booth-type spray system may clog resulting in less efficient pumping and possible under application of the skin treatment solution. Initially, the clog may not be significant enough to be immediately recognized. Thus, the spray system may continue to be operable but may provide incorrect flow rates and result in an inferior tanning experience. If the clog worsens, it may cause the pumping system to become inoperable and disable the spray booth during a spray tanning session of a paying customer.

SUMMARY

Embodiments disclosed herein propose a precision spray system for delivering a spray of skin treatment solution. The system includes at least one nozzle configured to emit a spray of skin treatment solution. A positive displacement pump is in fluid communication with the spray nozzle. The positive displacement pump includes a displaceable member, and displacement of the displaceable member corresponds to a pumping cycle of the positive displacement pump. A controller is in communication with the positive displacement pump. The controller is operable to apply a predetermined actuation parameter to direct an expected displacement and/or an expected displacement rate of the displaceable member and is also operable to receive an indication of an actual position of the displaceable member. The controller is further operable to compare the predetermined actuation parameter associated with the expected displacement of the displaceable member to a measured actuation parameter associated with the actual displacement of the displaceable member.

In certain embodiments, based on the comparison, either the positive displacement pump continues to cycle and/or a fault condition is indicated. In certain embodiments, a fault condition may be a warning that the comparison has yielded a result that is out of a first tolerance, which may be associated with a first level caution. The system may indicate the caution condition and still continue the pumping operation.

In certain embodiments, the positive displacement pump may be a piston-type pump that includes a stepper motor that functions as a linear actuator. The stepper motor linearly displaces the piston causing the pump to cycle. In this embodiment, the actuation parameter is associated with steps of the stepper motor. In an alternate embodiment, the actuation parameter may be electrical power applied to a non-stepper motor for a period of time, which may correspond to an actuation time. For example, electrical power may be applied to a D/C motor, an A/C motor, a speed controlled motor and the like.

Technical advantages of the system and method for precisely controlling and validating movements of a pump for a skin treatment spray system include the ability to detect underperformance of the pump in either pumping or siphoning. An operator may be warned of the underperformance and may take corrective action at an appropriate time. In addition, the underperformance of the pump may be monitored to determine if the underperformance worsens, and if so, corrective action may be taken by the operator, at an appropriate time when the pump is not in use during a spray session.

Further technical advantages include a pumping system that provides a steady, non-pulsed liquid flow for which the rate of flow and volume delivered may be precisely controlled and verified. Moreover, because solution is delivered in a single precisely controlled and maintained extension phase of the pump, calibration drift, that is common in conventional skin care treatment sprayer systems can be reduced or eliminated. In addition, because the pump system delivers liquid to a spray nozzle with minimum pre-pressurization time by extending a piston to pump the liquid, the pump system may reduce and/or eliminate problems associated with tolerance stack-up that occurs in conventional pumping systems.

Still further technical advantages include the ability to track the actual amount of solution being dispensed by the spray nozzles, as opposed to only being able to track the desired amount of solution dispensed. In accurately tracking the actual dispensed amount, the remaining content of a removable and replaceable container may more accurately be determined.

Other technical advantages will be readily apparent to one of ordinary skill in the art from the following figures, descriptions, and claims. Moreover, while specific advantages have been enumerated above, various embodiments may include all, some, or none of the enumerated advantages.

BRIEF DESCRIPTION OF THE DRAWINGS

A more complete understanding of the invention may be obtained by reference to the following drawings.

DETAILED DESCRIPTION

Figure 1:
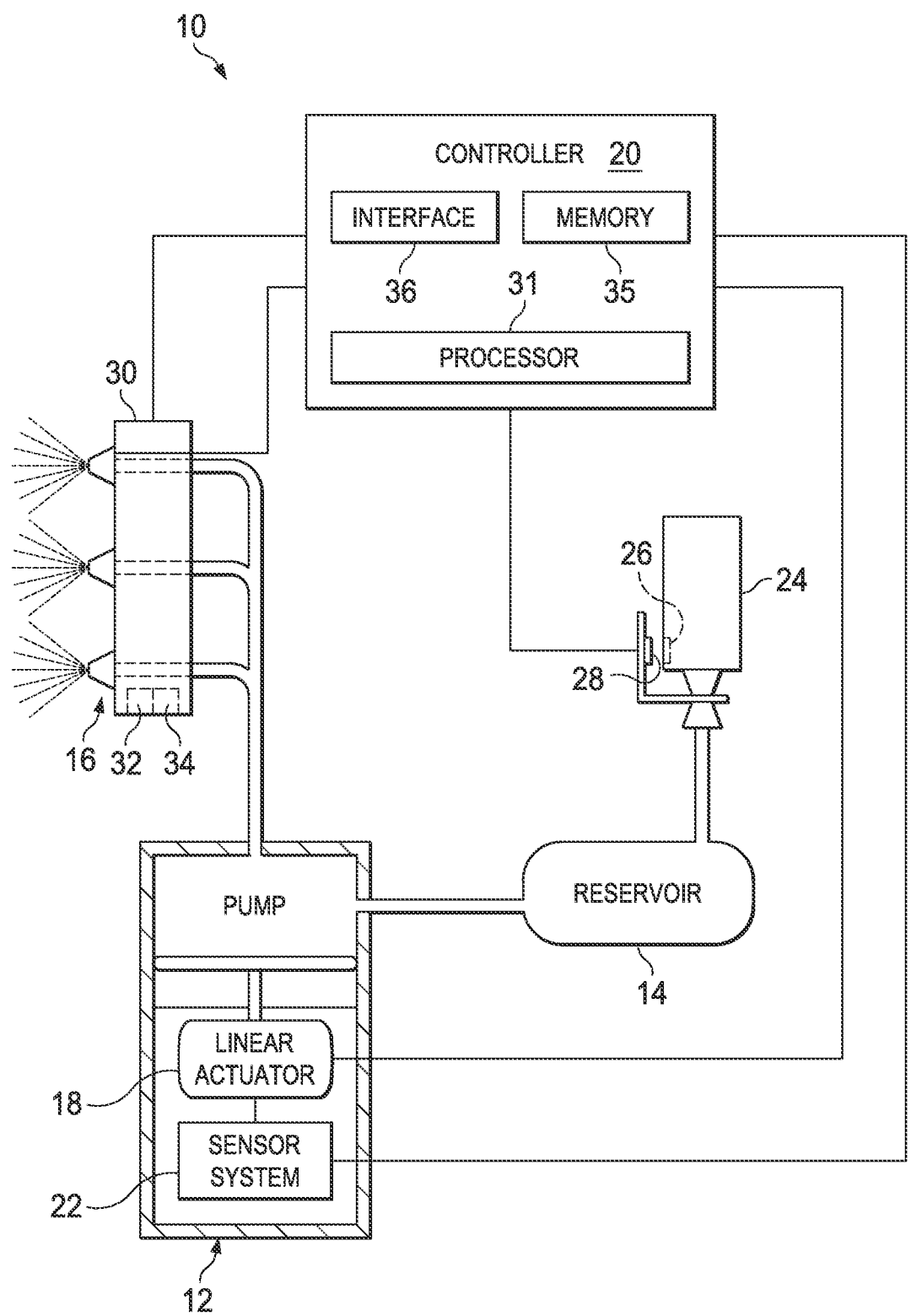
FIG. 1 schematically illustrates a precision spray pumping system adaptable for spraying a skin treatment solution.

FIG. 1 is a schematic illustration of a precision spray pumping system 10 according to embodiments of the present disclosure. The system 10 includes a positive displacement pump 12 that is operable to draw a liquid from a reservoir 14 and cause the liquid to be delivered to one or more spray nozzles 16. In certain embodiments, the spray pumping system 10 may not include a reservoir 14, and the pump will draw solution directly from a container, for example a removable container, of skin treatment solution. Any number of valves may be disposed among the fluid conduits connecting the reservoir 14, the positive displacement pump 12, and the spray nozzles 16. Valves, such as check valves, control the fluid flow including the flow direction.

The positive displacement pump 12 may be a piston pump powered by a linear actuator 18. The linear actuator 18 is in communication with a controller 20. The positive displacement pump 12 also includes a sensor system 22. The sensor system 22 is also in communication with the controller 20 and may communicate a signal to the controller 20 when the sensor detects a flag that corresponds to a particular position of a piston of the positive displacement pump 12. The detection of the flag corresponds to a home position of the piston.

The motor is actuated according to a predetermined actuation parameter that causes movement of the piston in the pump, which corresponds to delivery of a specific amount of liquid over a specific period of time. The actuation parameter may be any suitable control to cause movement of the piston by the linear actuator. For example, the actuation parameter may be applying power or a pulse or other motor activation method for a specified period of time to cause rotation of the rotor. In a preferred embodiment, the actuation parameter may be a pulse causing a rotor of a stepper motor to rotate a certain number of steps.

In one embodiment, the linear actuator 18 receives signals from the controller 20 and displaces the piston causing the liquid in the system 10 to be either siphoned or pumped. During a pump cycle the pump 12 receives a signal from the controller 20 that is intended to cause a predetermined expected distance of travel to extend the piston. A second signal is communicated from the controller 20 and directs the motor to reverse direction and retract the piston until an actual position of the flag, and thus the piston, is detected by the sensor 22. By comparing the steps taken by the linear actuator 18 during the extension phase of the cycle to the steps taken by the linear actuator 18 during the retraction (siphon) phase of the cycle, a determination may be made whether the piston traveled the expected distance in each phase of the cycle. If it is determined from the comparison that the piston did not travel an expected distance in one of the phases, and it is determined that the difference determined by the comparison is outside an acceptable tolerance, the system 10 provides an indication that a fault has occurred. The fault may indicate a blockage in the liquid conduit system that prevented the expected displacement of the piston in the positive displacement pump 12. The difference in steps between each cycle phase is checked against a permissible variance or tolerance in determining whether to indicate a fault condition, and furthermore what fault condition to indicate.

The reservoir 14 receives a liquid from a container 24. Any suitable number or type of valves may be disposed in the conduits between the reservoir 14 and the container 24 to control the fluid flow. According to certain embodiments, the container 24 is a removable bag-in-box container containing a skin treatment solution. The bag-in-box container 24 includes a tag 26 that is machine readable, such as a radio frequency identification (RFID) tag, bar code, QR (quick response) code, and the like. The tag 26 communicates information stored on or otherwise readable from the tag 26 to an interrogator 28.

The interrogator 28 is in communication with the controller 20 and receives information regarding the container 24 and the solution therein and directs control of the precision pumping system 10 based on that information. For example, the interrogator 28 may receive information indicating that the solution within the container 24 has a high viscosity. The controller 20 uses this information to direct an appropriate displacement of the piston to pump a specific volume of the high viscosity solution. The proper displacement of the piston will cause an expected spray output from the spray nozzles 16. In this manner, a removable container 24 of skin treatment solution is received by the precision spray pumping system 10, and the solution may be sprayed through one or more of the nozzles 16 and applied to the skin of an individual in a skin treatment booth, such as a spray tanning booth.

In addition, the controller 20 may also control a gantry 30. The gantry 30 supports and moves the spray nozzles 16. The gantry 30 translates linearly to any position between an upper limit position and a lower limit position (and/or side-to side limits) to direct spray from the nozzles 16 to particular body parts of the person standing in the spray tanning booth. The control and movement of the gantry 30 is coordinated by the controller 20 such that a displacement of the piston in the piston pump 12 correlates to a specific distance of travel of the gantry 30. For example, if the gantry 30 is to provide a skin treatment solution to just the legs of an individual standing in a spray tanning booth, a full displacement of the piston from a retracted position to an extended position is coordinated with the movement of the gantry 30 to pass over the legs of the individual. The controller 20 also receives signals from a height sensor 32 that optically or otherwise senses the height of an individual in the spray tanning booth and can adjust the travel of the gantry 30 accordingly. Other sensors, such as a linear or rotational encoder, or a time or limit switch corresponding to a particular position or motion of the gantry 30, may also be in communication with the controller 20 to provide information regarding the actual position of the gantry 30, which, similar to the piston position, may be compared to an expected position determined by the controller 20.

Operation of the pump 12 generally corresponds with a spray treatment session. A spray treatment session may include one or more spray treatments, which may include one or more spray passes. Generally, a treatment may be associated with a specific solution and a pass may be associated with the gantry passing over a specific part of the customer's body and spraying skin treatment solution. For example, an individual may desire a spray treatment session to receive a spray tan. The customer may receive a first spray treatment of bronzer tanning solution delivered through the nozzles. The bronzer may be sprayed in a first pass, then the customer may be instructed to rotate 90 degrees to receive a second spray pass, then rotate 90 degrees to receive a third pass, then rotate 90 degrees to receive a fourth pass. After receiving the bronzer tanning solution, the customer may receive a moisturizer solution, which may include two spray passes over the entire body of the customer. Each spray pass may correspond to the customer rotating to receive the moisturizer on the front (facing the nozzles), then on the back of the customer. Finally, the customer may receive a second face treatment corresponding to a single pass of the nozzles over the face of the customer.

Between spray passes, the pump may retract to siphon additional liquid from the reservoir. This siphoning may correspond to a pause in the spray cycles. In certain embodiments, the siphoning corresponds to a dry pass of the gantry supporting the nozzles. Generally, no liquid is dispensed from the nozzles during a dry pass. The dry pass may or may not correspond to the system blowing air to dry the body. Thus, the operation of the pump is to extend the piston to spray solution, then to retract the piston to siphon liquid from the reservoir during a time when it is not necessary for the pump to spray. The time of each phase (pumping and siphoning) may be different and may be any suitable time desired for the spraying of skin treatment solution. For example, the pump may deliver a specific quantity of solution over a period of approximately 6.5 seconds. Then the siphoning phase may be quicker, such as three seconds. The siphoning phase may correspond to an instruction and delay for the customer to change their body position, which may be approximately twelve seconds. Or the siphoning time may be shorter and correspond to a dry pass of the gantry to prepare it for a subsequent spray pass over the customer. Siphoning occurs when the spray is not-desired and the pump is not spraying, such as a delay or a dry pass associated with a spray tanning operation.

The controller 20 includes one or more processors 31 and memory 35. Thus, the controller is essentially a microprocessor or other logic controller in communication with at least temporary memory and functions to control the components used in the spray session and to communicate data to other components of the system 10. In certain embodiments, the controller 20 may employ an Android or other suitable operating system, such as iOS. The controller 20 may also be in communication with an interface 36. The interface 36 may be integral with or remote to the controller 20. The interface 36 may be any suitable interface that allows a human to interact with and receive information from the controller 20. In certain embodiments, the interface 36 may be a touch-screen, keypad, monitor, and the like. In a preferred embodiment, the interface 36 may be a touch-screen that allows the user to communicate with the controller 20 by touching the screen where command icons and other information are displayed. The interface 36 may also be used to program the controller 20 or provide other information to the controller 20 that may be used to operate the precision spray pumping system 10.

Figure 2A:
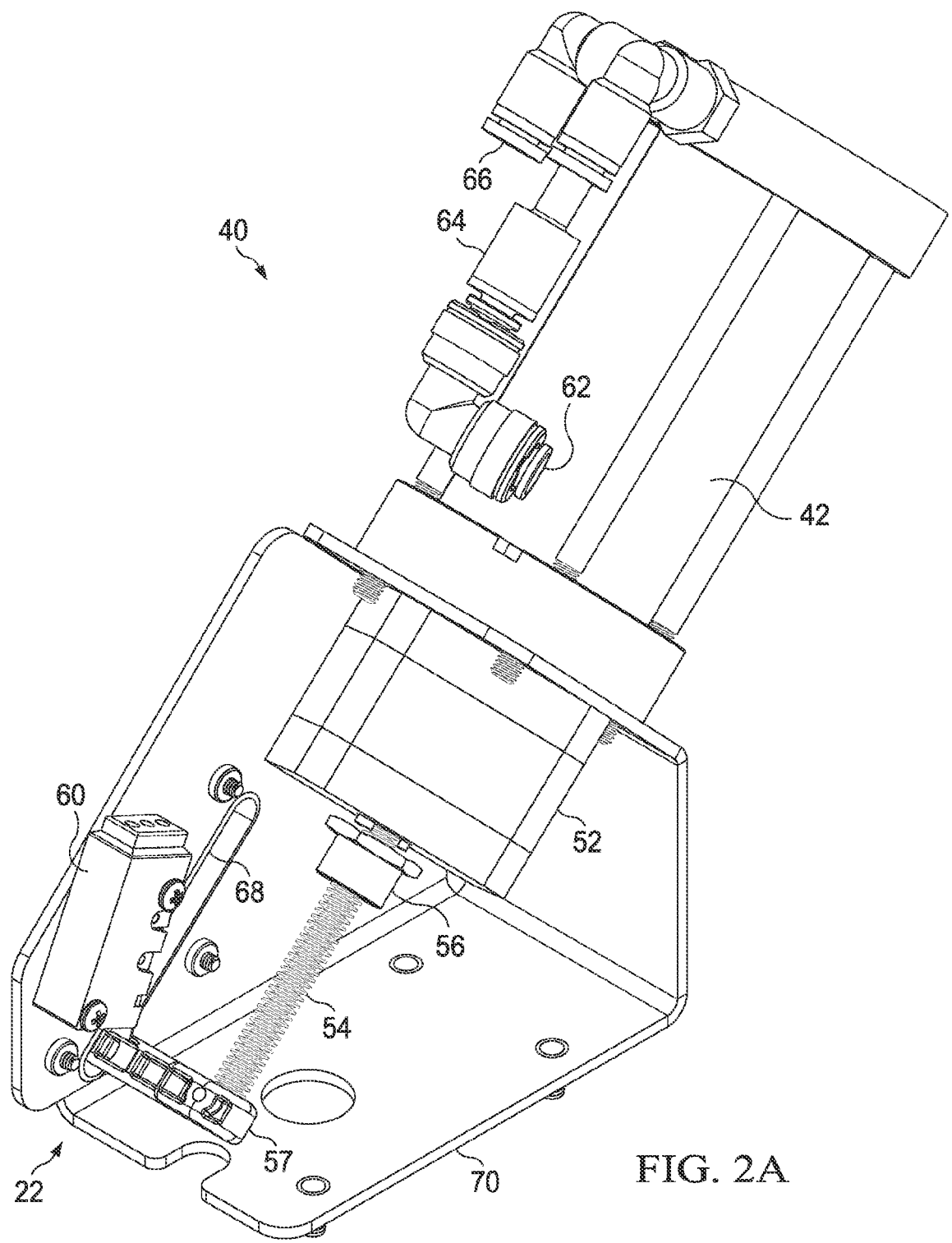
FIG. 2A is an isometric view of a precision piston-type pump system with a piston in a refracted position.
Figure 2B:
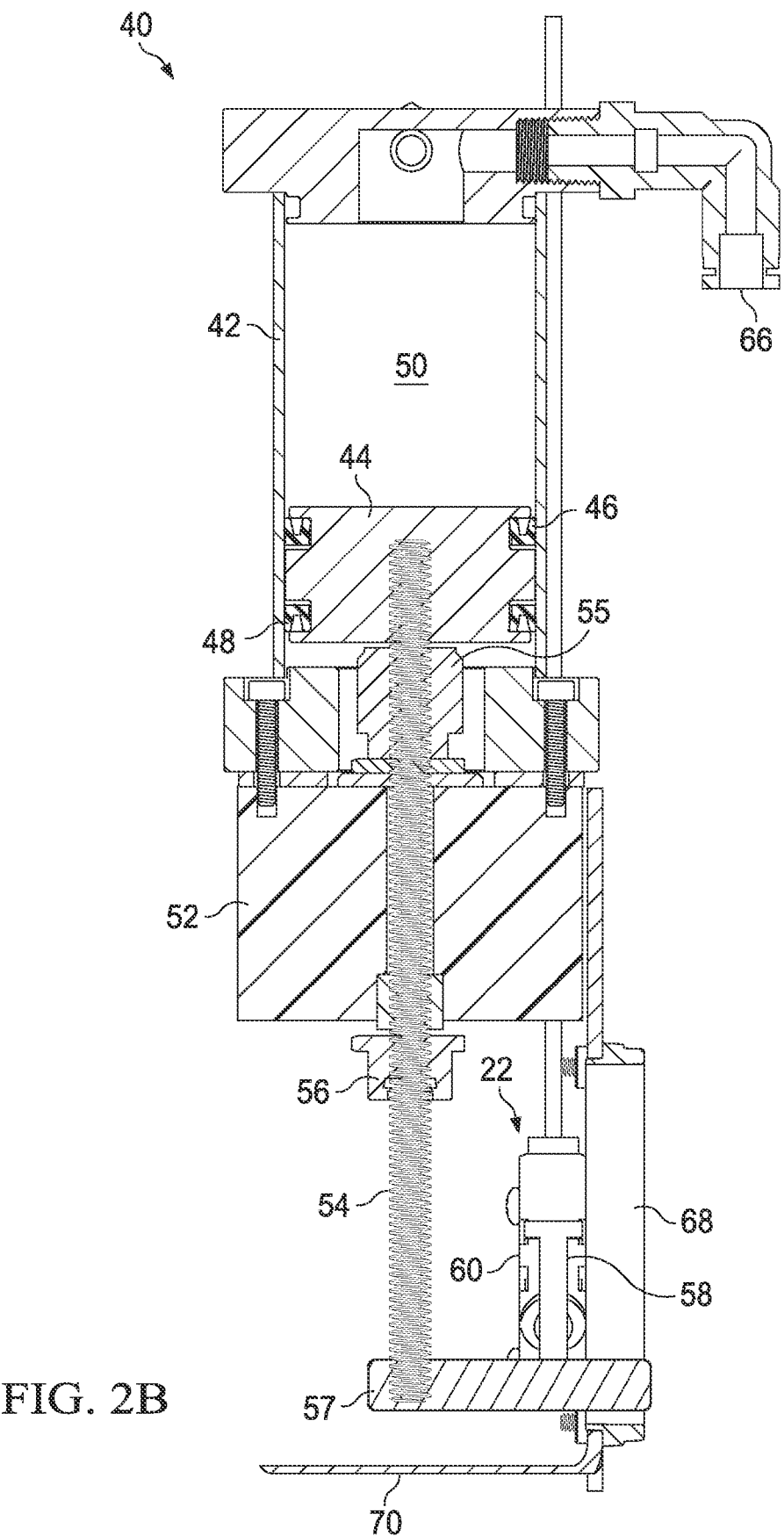
FIG. 2B is a cross sectional view of the precision piston-type pump system of FIG. 2A.

FIGS. 2A and 2B illustrate an isometric and a cross-sectional view, respectively, of an embodiment of a positive displacement pump as indicated in FIG. 1. The positive displacement pump is a precision pump system 40, which ensures that a precise quantity of liquid is delivered to the spray nozzles 16. In certain embodiments, the precision pump system 40 may pump approximately 25 ml over a time period of 4 to 25 seconds. In certain embodiments, the precision pump system 40 may pump approximately 25 ml over approximately 6.5 seconds. This flow rate may correspond to a pass of the gantry 30 and the spray nozzles 16 over a portion of the body. For example, the gantry 30 may start at the head of a person and travel downward to the person's feet over a time of 6.5 seconds and simultaneously spray approximately 25 ml of spray tanning solution. The given values are only examples, and it should be understood that the system is operable to pump any suitable volume of solution over any suitable time.

A preferred embodiment of the present disclosure employs a piston-type pump which delivers a pulse-free spray, which is particularly applicable to spray tanning operations as discussed in U.S. Pat. No. 7,007,407 to Cooper, the disclosure of which is hereby incorporated by reference. Alternatively, the spray system of the present invention could use a multi-line peristaltic pump, a solenoid pump, a diaphragm pump, a reciprocating piston pump, a centrifugal pump, or vane pump, either alone or in combination with each other and/or the piston-type pump disclosed herein.

According to a certain embodiment, the precision pump system 40 includes a cylinder 42 and a piston 44. The piston 44 is a displaceable member that travels linearly within the cylinder 42 creating a pressure and volume differential, which siphons liquid from a reservoir and pumps it through the conduits to the spray nozzles 16 during a spray pumping cycle. The cycle includes a siphoning phase and a pumping phase. The piston 44 includes an upper seal 46 and a lower seal 48. The upper seal and lower seal 46 and 48 may be an O-ring type seal or other seal employing resilient material that ensures that a fluid chamber 50 within the cylinder is liquid-tight such that the liquid is prevented from escaping around the piston 44. The precision pump system 40 may include only one seal; however multiple seals allows one to serve as a primary seal and another seal to server as a backup seal for improved reliability.

Displacement of the piston 44 is directed by a suitable linear actuator. The linear actuator according to an embodiment of the present disclosure includes a stepper drive motor 52. In certain embodiments, the stepper drive motor 52 causes a lead screw 54 to be linearly displaced a certain distance based on signals received by the motor 52. The signals correspond to a known angular displacement of a rotor of the motor 52 and the corresponding displacement of a rotor drive nut 55. The rotor drive nut 55 may be disposed within the cylinder 42 or outside of the cylinder 42. In the illustrated embodiment, the rotor drive nut 55 is disposed within the cylinder 42 and an alignment bushing 56 is disposed outside the cylinder 42. The lead screw 54 extends through the motor 52. The rotor drive nut 55 meshes with corresponding threads of the lead screw 54 such that a specified rotation of the rotor drive nut 55 by the rotor causes a corresponding linear displacement of the lead screw 54 and the piston 44 attached to an end of the lead screw 54. In an alternate embodiment, the rotor drive nut 55 may be disposed on an opposite side of the motor 52, for example, the alignment bushing 56 may be replaced by the rotor drive nut 55.

Figure 3A:
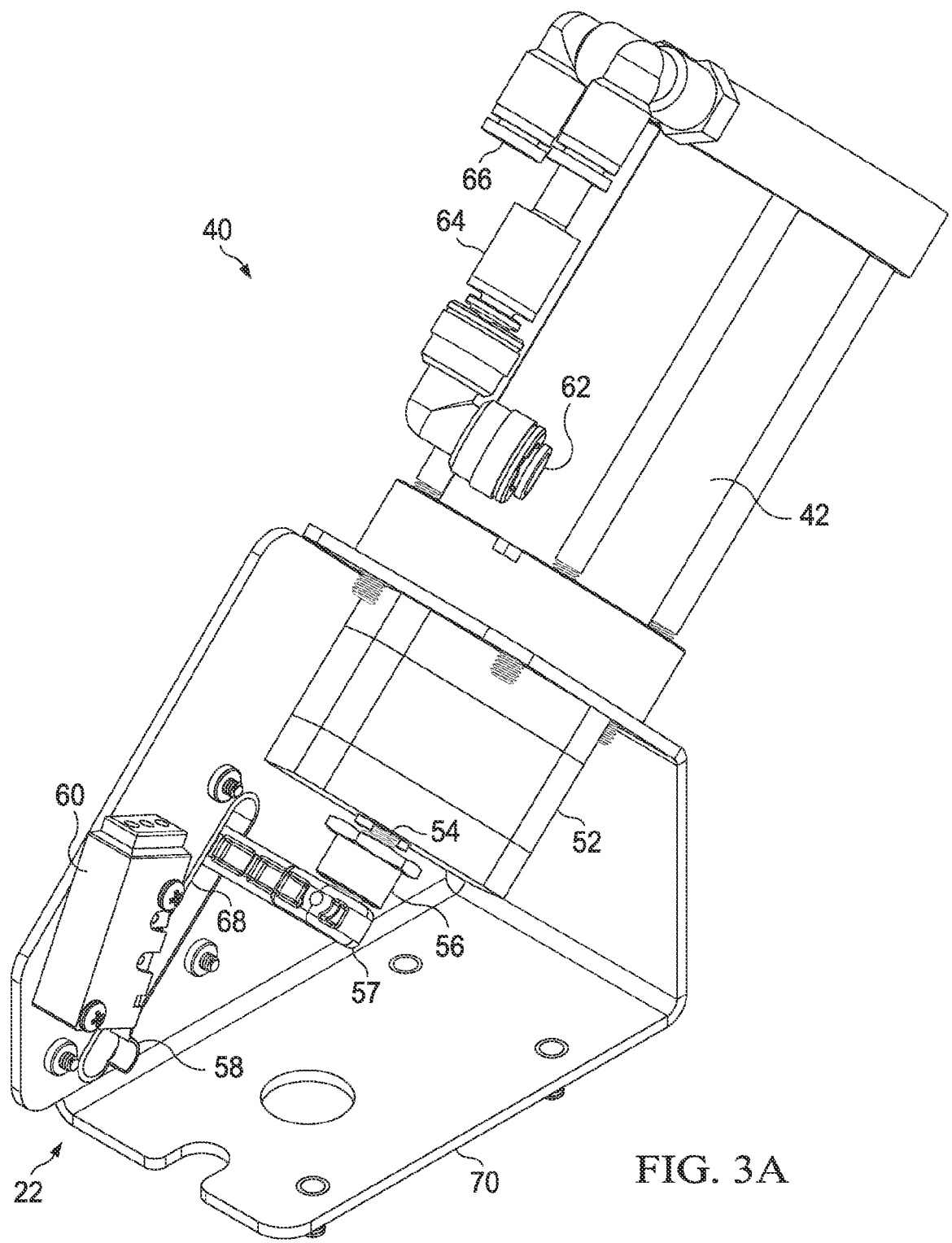
FIG. 3A is an isometric view of a precision piston-type pump system with a piston in an extended position.
Figure 3B:
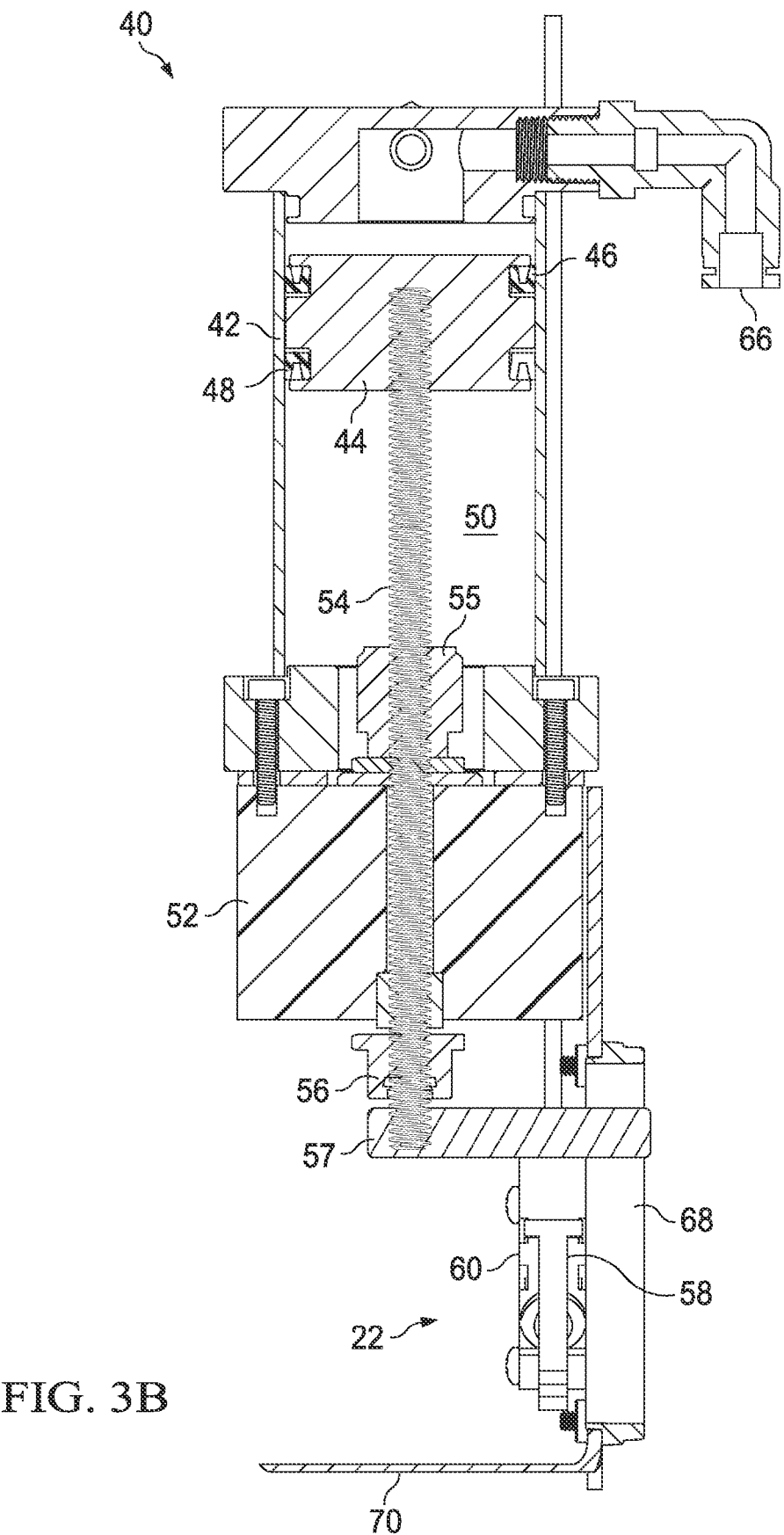
FIG. 3B is a cross sectional view of the precision piston-type pump system of FIG. 3A.

As the motor 52 of the linear actuator drives the piston 44 from the extended position shown in FIGS. 3A and 3B to the retracted position shown in FIGS. 2A and 2B in the siphoning phase of the pump cycle, the fluid chamber 50 fills with solution from the solution reservoir 14. In the illustrated embodiment, the retracted position corresponds to a maximum volume of the fluid chamber 50, and the extended position corresponds to a reduced volume of the fluid chamber 50 from the retracted position that occurs when the liquid is being pumped. The liquid is siphoned and pumped as the piston 44 cycles between the retracted and extended position or any suitable intermediate positions as required by the desired fluid rate.

The solution is drawn through an inlet 62 and through one or more check valves 64. The check valves 64 ensure that the liquid flowing through the inlet 62 into the fluid chamber 50 only flows in one direction because the pressure from the liquid flowing the opposite direction closes the valve and blocks liquid flow from such opposite direction. The piston 44 travels from the retracted position to the extended position and displaces the liquid in the fluid chamber 50 so that it exits the precision pump system 40 through an outlet 66. The liquid may travel through one or more check valves after it leaves the outlet 66. The check valve on the outlet side of the liquid system performs similarly as the check valve 64 on the inlet side to ensure that liquid only travels one direction through the liquid system. Other types of direction control valves, such as solenoid valves, may be used to control of liquid through the system. The outlet 66 on the top of the pump facilitates dispelling unwanted air with minimal priming of the pump.

According to the teachings of the present disclosure, a piston-type pump as describe herein may reduce and/or eliminate the need for solenoid valves as a control for the delivery of the liquid to the spray nozzles. Thus, the piston pump reaches its pumping pressure quickly and solution can be delivered virtually simultaneously with the displacement of the pump. Also, the solution may cease being delivered virtually simultaneously with the ceasing of the extension of the piston.

Attached at an opposite end of the lead screw 54 from the piston 44 is a flag 57. The flag 57 is a component of the position sensor system 22, as shown and described with respect to FIG. 1. Because the flag 57 is attached to the lead screw 54, it is linearly displaced the same distance as the piston 44 when the linear actuator 52 is operated to siphon or pump liquid to one or more spray nozzles 16 according to the teachings of the present disclosure. In one embodiment, motion of the flag 57 and thus the lead screw and the piston 44 is constrained by a slot 68. In addition, the coupling of the slot 68 and the flag 57 prevent the lead screw 54 from turning and also prevent the piston 44 from rotating. The flag 57 also serves as a visual indicator of the displacement of the piston 44 within the cylinder 42.

Figure 5:
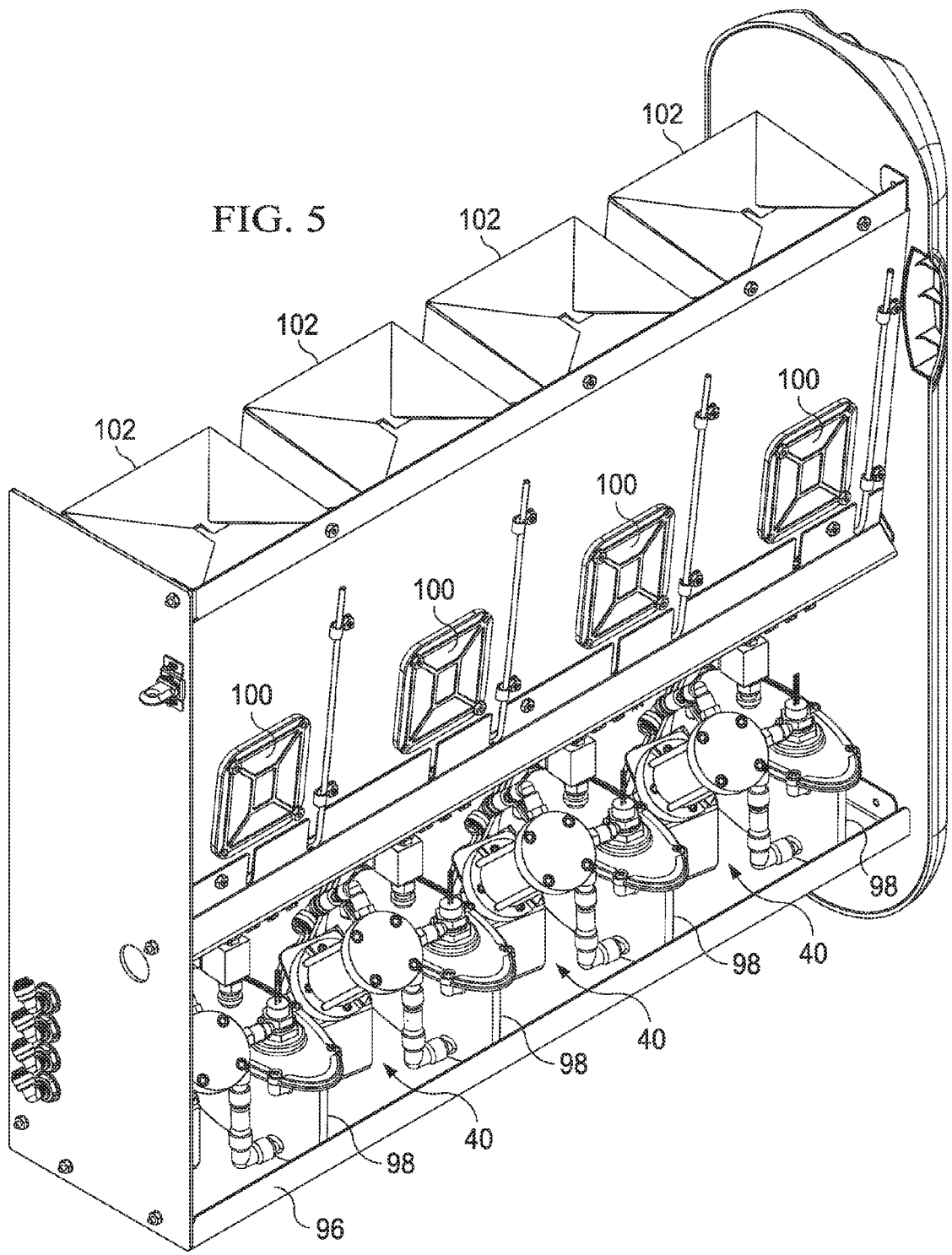
FIG. 5 is a portion of a spray tanning system employing a plurality of precision spray pumping systems according to embodiments of the present disclosure.

The slot 68 is formed in a panel of a mounting bracket 70. The mounting bracket 70 is a metal or plastic bracket with features to attach the precision pump system 40 to a drawer of a spray tanning booth as shown in FIG. 5. In certain embodiments, the mounting bracket 70 may be an angled mounting bracket which holds the precision pump system at a predetermined angle.

As shown in FIGS. 2A and 2B, when the piston 44 is in a retracted position, the flag 57 displaces an arm 58 of a sensor 60. Displacement of the arm 58 creates an electrical contact with the sensor 60. The electrical contact is communicated to the controller 20, which determines that the piston 44 is in a known retracted or home position as shown in FIGS. 2A and 2B.

FIGS. 3A and 3B show isometric and cross section views, respectively, of the precision pump system 40 in a piston extended position. The precision pump system 40 has this orientation once the pump has completed the pumping phase of its cycle and the liquid has been directed from the fluid chamber 50 through the conduit and to the spray nozzles 16. As shown in FIGS. 3A and 3B, the flag 57 is displaced away from the sensor 60, and thus the arm 58 is not displaced by the flag 57. In the next phase of the cycle, where the piston 44 retracts, the flag 57 displaces the arm 58, thus the position of the flag 57 and the piston 44 is sensed, and electronically communicated to the controller 20 such that the controller determines that the piston is in its known fully retracted position. In other embodiments, other types of proximity sensing means may be used. For example, the sensor may be a mechanical limit switch as shown, or may be a magnetic device or any other device for sensing the position and proximity of a mechanical component, such as a pump piston.

As explained in more detail below with respect to FIG. 4, the number of motor steps to move the piston 44 to the known retracted position may be compared with the number of motor steps that previously moved the piston 44 to an expected extended position, and a determination of whether a fault has occurred may be made based on that comparison. According to an alternate embodiment, the position sensor may be configured such that the extension of the piston, as opposed to the retraction of the piston, is detected by the sensor and considered the home position.

In the case of the stepper motor illustrated, the motor may be configured to slip. That is the rotor may be directed to turn in response to a received pulse, but the piston will not displace. Thus, an incomplete blockage in the liquid line may result in an initial displacement of the piston, and then the motor 52, or a part of the piston drive system, may slip, skip, or stall as the piston 44 is opposed by the increased pressure created by the blockage. In the subsequent pump phase, the motor steps to retract the piston 44 until the flag 57 is detected by the sensor 60 at the fully retracted home position are determined. Thus, the number of motor steps intended to be taken by the motor to extend the piston a known distance to deliver a particular quantity of skin treatment solution can be compared to the number of motor steps actually taken to return the piston 44 to the home position where the flag 57 is detected. From this comparison, the steps taken by the motor in the extension phase that did not result in a displacement of the piston may be determined, which provides an indication of the severity of the blockage. In other embodiments, the motor may be configured to stall or slow down when the piston is opposed by a predetermined force. In still alternate embodiments, a clutch mechanism may be employed to allow the motor to rotate without displacing the piston when the piston is opposed by a predetermined force in the fluid line.

Figure 4:
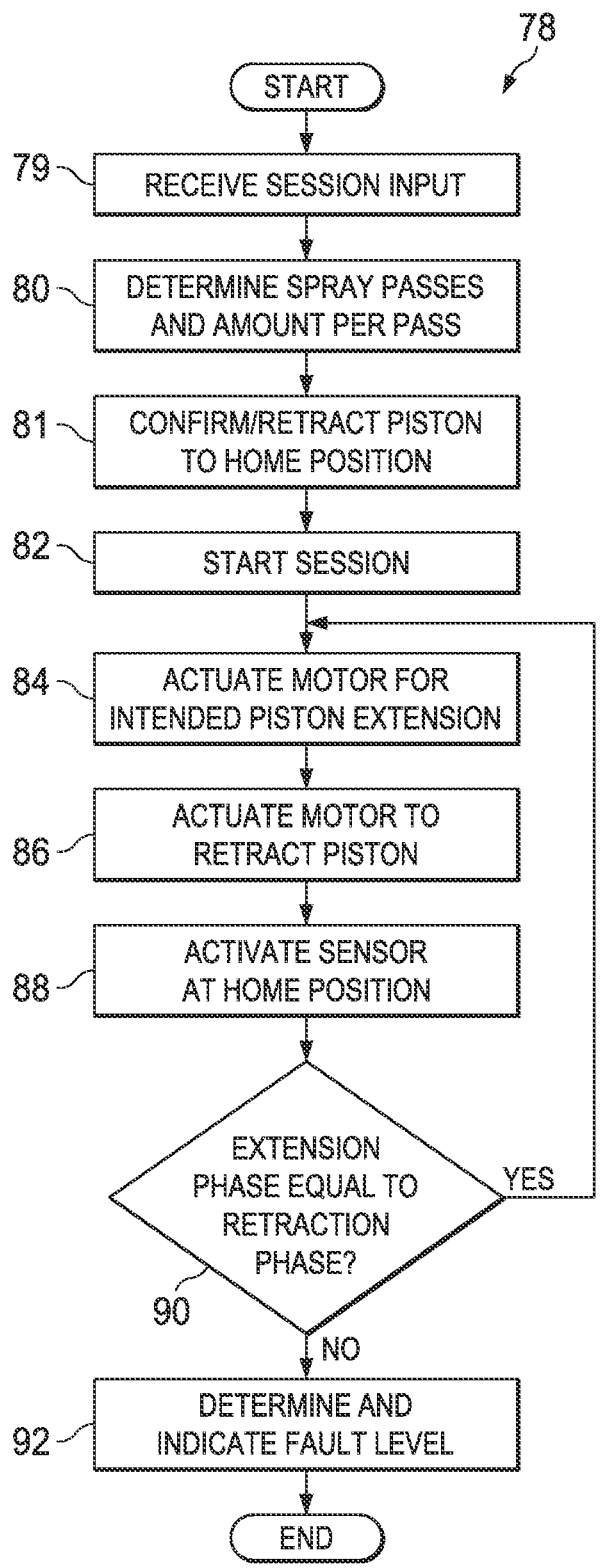
FIG. 4 is a flow diagram of a method of operation for a precision spray pumping system.

FIG. 4 is a flow diagram of a method 78 of operation of the precision spray pumping system according to an embodiment of the present disclosure. The method 78 begins at step 79 where session input is received by the controller. A user may build a skin treatment session by inputting certain desired spray treatments, certain levels of treatment corresponding to an amount of skin treatment solution to be sprayed by the system, and a particular part of the body or the whole body over which the gantry will travel as the skin treatment solution is sprayed. The user may provide such input for multiple treatments to be provided by the sprayer during a session.

At step 80, the controller determines the number of spray passes to perform and the amount of solution to deliver during a spray pass. This determination is based on the session input provided by the user. Generally, a spray pass corresponds to a single extension of the pump, which delivers the skin treatment solution to the nozzles and is sprayed onto the person in the skin treatment booth as the gantry moves to allow the spray from the nozzles to coat a particular part of the body. The single extension of the pump allows a non-pulsed spray to be delivered over a certain time period, such as 6.5 seconds. This non-pulsed spraying of the skin treatment solution is referred to as a spray pass. A treatment with a skin treatment solution typically includes multiple spray passes over a designated part of the body. For example, the user receives one spray pass of a spray tanning solution over the front of her whole body. Then, as part of the same treatment, the user is instructed to turn 90 degrees and receive another spray pass of the spray tanning solution over the side of her body. Thus, the controller receives the input regarding the desired treatments and determines the number and the sequence of spray passes to perform.

At step 81, the piston is confirmed to be in its retracted, home position. As previously described, the retracted position of the piston activates a sensor, which communicates to the controller that the piston is in the home position. If the piston is not in its home position, it is retracted and the cylinder of the pump is filled with skin treatment solution and until the flag is detected and the piston is confirmed to be in its known, home position. From the known, home position, information about the travel of the piston during the extension and subsequent retraction phases of the pump cycle can be determined and compared. If the home position is not reached after a predetermined period of time or after a predetermined number of attempts, the controller may indicate an error condition.

The system starts the session according to the input of the user, at step 82. The user may initiate the session after entering the skin treatment spray booth and touching a touch-sensitive sensor to provide input to the controller that the user is in position and ready to receive the spray session.

At step 84, the motor is actuated according to a predetermined actuation parameter intended to extend the piston 44 and pump a specific amount of liquid over a specific period of time or a specific movement distance of the piston 44, which corresponds to a spray pass of the gantry over a part or the whole body. Precise and consistent application of a skin treatment solution is achieved according to the teachings of the present disclosure. For example, a precise and consistent volume of skin treatment solution is dispensed by the pumping system. By confirming the extension and refraction phases of a pump are equal within a certain acceptable tolerance, less than 5% volume variation in spray passes may be achieved. In certain embodiments, the volume variation in spray passes is less than 1%.

The session input determines the magnitude of the actuation parameter, which may be any suitable control to cause movement of the piston 44. For example, the actuation parameter may be applying power or a pulse or other motor activation method for a specified period of time to cause rotation of the rotor. In a preferred embodiment, the actuation parameter may be causing a rotor of a stepper motor to rotate a certain number of steps. Actuation of the motor using the predetermined actuation parameter causes displacement of the piston, which should be a desired displacement to extend the piston 44. The predetermined number of steps (or time, etc.) causes an expected angular displacement of a rotor within the motor, which corresponds to an expected displacement distance of the piston 44 during a pumping phase of the pump's cycle. However, if there is a force greater than a predetermined value, the motor or other drive system will slip or stall and the intended displacement of the piston 44 will not correspond to the actual displacement of the piston 44.

At step 86, the motor is actuated in steps (or time or otherwise) to retract the piston and draw skin treatment solution into the pump in connection with a second (siphoning) phase of the pump's cycle. The piston is retracted while another action is occurring. For example, the piston may retract while the gantry moves to be in position for another spray pass. Or, the piston may retract during a time period in which the user is given a short amount of time to rotate to be in position to receive another spray pass over the side of her body.

The piston is retracted until the sensor is activated at step 88. As described herein, activating the sensor includes displacement of an arm to create an electrical connection, which is communicated to the controller 20.

At step 90, the controller determines if the extension pump phase is approximately equal to the retraction pump phase. For example, it is determined whether the predetermined actuation parameter, for example the number of steps (or distance or time) associated with retracting the piston is approximately equal to the predetermined number of steps (or time, etc.) used to extend the piston. In normal operation, the predetermined actuation parameter needed to retract the piston to activate the sensor should be approximately equal to the predetermined actuation parameter used to extend the piston, as described with respect to step 84. The number of steps for retraction may be within an acceptable range, tolerance, or variance but may not be exactly equal to the predetermined number of steps to extend the piston and the controller may determine that the retraction steps are approximately equal to the extension steps. In certain embodiments, the actuation parameter may be associated with rotation or linear movement of an encoder. The actuation parameter may also be steps of a stepper motor or electrical motor power applied over a period of time to an AC or DC motor, which may or may not have speed control.

If it is determined that the retraction actuation parameter is approximately equal (within an acceptable tolerance) to the extension actuation parameter, the pump will continue to cycle and the method returns to step 84, and the system is prepared to deliver skin treatment solution for another spray pass. If it is determined that the actuation parameter to retract the piston is not equal (within an acceptable tolerance) to the actuation parameter used to extend the piston, then a fault level may be determined and indicated at step 92. The system may take any suitable controller and/or mechanical action in response to a particular fault level determination including, but not limited to, continue pumping, ceasing pumping, and/or sending a communication notifying a service technician of the fault.

The fault level may be a first caution level, a second caution level, or a severe fault level, which may correspond to one or two yellow LED indicators and/or a red LED indicator. In other embodiments, the fault level may be displayed by the interface. As an example, the expected extension of the piston may have been intended to cause the delivery of 20 ml of solution to the nozzles. After retracting the piston and making the comparison, it may be determined that the piston only extended a distance sufficient to delivery 18 ml of solution, each step of the motor corresponds to the delivery of a fraction of a milliliter of solution. The difference of 2 ml may be sufficient to provide a first caution indicator but allow the pump to continue operation to avoid inconveniencing the customer during the middle of a spray tanning session. However, if the pump actually only delivered 10 ml of solution, this may correspond to a severe fault warranting shut down of the pump from continued operation.

By tracking multiple caution levels, it may be determined if the malfunction in delivery continues to worsen, which may be an indicator of a clog in the liquid lines, a malfunctioning valve, or may be an indication of a malfunctioning pump. In addition, the controller may communicate the fault indicator to a service technician via email or other electronic communication method.

If the number of steps used to retract the position to activate the sensor is less than the predetermined number of steps used to extend the piston, it may be determined that a blockage in the liquid system prevented the piston from fully extending. Thus, it may be determined that there is a clog in the liquid system upstream of the pump.

If the number of steps to retract the piston is greater than the number of steps to extend the piston, it may be determined that more steps and motor power was required to retract the piston to activate the sensor than was expected. In this instance, it may be determined that the pump system has erred in its siphoning phase. Accordingly, this fault condition may likewise be indicated by the controller. The method ends after either a fault or a caution level is indicated and/or a go condition is determined and the pump continues to cycle. Of course, the method also ends upon the successful and/or fault-free completion of the predetermined number of pump cycles as determined by the spray treatment session being delivered. The comparison operation is employed during each pumping cycle, which allows precise delivery of a specific amount of skin treatment solution during each spray pass. Also, the precision pump method 78 may be initiated by an operator in a single instance to assist in diagnosis of a possibly malfunctioning system. In addition, the system may indicate that the piston did not return home if the sensor is not activated within a predetermined time limit.

Thus, the precision pump system according to embodiments of the present disclosure delivers consistent sprayed solution from the nozzles. When spray tanning solution, such as a bronzer, is sprayed from the nozzles, the user receives repeatable and consistent results in darkness/color level for each spray pass, for each spray treatment, and for each spray session.

Consistent with the teachings of the present disclosure, other sensing systems then that described herein may be used to detect a position of the piston. For example, the position of the piston may be determined using a linear or rotational encoder. In an alternative embodiment, the position of the piston may be determined by a timer.

FIG. 5 illustrates a particular embodiment of a precision spray pumping system used in connection with a spray skin treatment booth, such as a tanning booth. As shown, four precision pump systems 40 are supported by a support structure 96. Each pump system 40 is in fluid communication with a respective reservoir 98. In addition, the precision pump system 40 is in electronic communication, through a controller, with a respective interrogator 100. The interrogator may read information stored on a machine readable tag, such as an RFID tag, attached to a removable container 102 of skin treatment solution, such as a spray tanning solution. The information or data the interrogator 100 reads from the RFID tag may be used by the controller to direct operation of the pump system 40. The removable container 102 may contain any type of solution used in the application of a cosmetic to the skin in a spraying operation. For example, the solution may be a solution for pre-tanning, moistening, tanning, and post-tanning. The solution may be clear or bronze and may be water or oil based.

Each of the pump systems 40 may be plumbed to allow solution to be pumped from a respective reservoir 98 to the plurality of spray nozzles 16 (as shown in FIG. 1). In this manner, each pump may be operable to pump a different solution to the spray nozzle 16. Thus, an individual may receive a spray skin treatment session, such as a spray tanning session that includes treatment from a plurality of different skin treatment solutions. For example, the individual may receive a pre-tanning solution in a first treatment operation from a first reservoir pumped by a first pump system 40. The same person, in a second subsequent treatment operation, may receive a bronzer skin treatment solution pumped by a second precision pump system 40 and sprayed on the individual. Each spray precision pump system 40 is operable as described herein to detect a predetermined position of its piston and communicate that information to a controller, which can then use that information in a comparison operation for fault detection to ensure optimum pump performance.

According to an alternate embodiment, a single positive displacement pump according to the teachings of the present disclosure may siphon solution from a plurality of containers and/or reservoirs. Which solution is siphoned may be controlled by a solenoid or other type of valve. The pump phase may correspond to a delivery of a solution to one or more nozzles. In this embodiment, the pump may be physically positioned near the nozzles to minimize the amount of solution that may remain in the liquid conduit lines after one solution is delivered and when switching to a second solution.

The invention claimed is:

1. A precision pumping system for delivering a spray of skin treatment solution, comprising:
   at least one nozzle configured to emit a spray of a skin treatment solution;
   a positive displacement pump in fluid communication with the at least one spray nozzle, the positive displacement pump comprising a displaceable member, displacement of the displaceable member corresponding to a pumping cycle of the positive displacement pump;
   a controller in communication with the positive displacement pump, the controller being operable to apply a predetermined actuation parameter to direct an expected displacement of the displaceable member and being further operable to receive an indication of an actual position of the displaceable member;
   a flag coupled to the displaceable member; and
   a position sensor operable to detect the flag;
   wherein the controller is further operable to compare the predetermined actuation parameter associated with the expected displacement of the displaceable member to a measured actuation parameter associated with the actual displacement of the displaceable member.

2. The system of claim 1, wherein the predetermined actuation parameter is associated with steps of a stepper motor.

3. The system of claim 1, wherein the predetermined actuation parameter is associated with electrical power applied for a period of time to a linear actuator.

4. The system of claim 3, wherein the linear actuator comprises a motor.

5. The system of claim 1, wherein the positive displacement pump comprises a piston pump and the displaceable member comprises a piston.

6. The system of claim 5, further comprising a linear actuator operable to displace the piston.

7. The system of claim 6, wherein the linear actuator comprises a motor.

8. The system of claim 7, wherein the motor comprises a stepper motor.

9. The system of claim 1, further comprising a linear actuator operable to direct motion of a lead screw, the lead screw having a piston coupled to a first end and the flag coupled to an opposite end, the detection of the flag corresponding to the actual position of the displaceable member.

10. The system of claim 9, further comprising a mounting bracket defining a guide slot constraining a linear motion of the flag.

11. The system of claim 1, wherein the position sensor comprises an arm and displacement of the arm by the flag generates an electrical signal associated with the actual position of the displaceable member.

12. The system of claim 1, wherein the positive displacement pump delivers the skin treatment solution to the at least one spray nozzle.

13. A precision sprayer system for spraying a skin treatment solution, comprising:
   a piston pump comprising a piston and a linear actuator, the linear actuator operable to displace the piston during a pumping cycle of the piston pump;
   a position sensor operable to detect a flag coupled to the piston, detection of the flag corresponding to a known position of the piston;
   a controller in communication with the linear actuator, the controller being operable to apply an actuation parameter to direct a displacement of the piston and being further operable to receive a signal from the position sensor upon detection of the flag;
   at least one sprayer nozzle receiving a skin treatment solution from the piston pump; and
   wherein the controller is further operable to compare a predetermined actuation parameter associated with an expected displacement of the piston to a measured actuation parameter associated with an actual position of the piston.

14. The system of claim 13, wherein the linear actuator comprises a stepper motor and the actuation parameter is associated with steps of the stepper motor.

15. The system of claim 14, wherein the linear actuator comprises a motor and the actuation parameter is associated with a current for a period of time received by motor.

16. The system of claim 13, further comprising a mounting bracket defining a guide slot constraining a linear motion of the flag.

17. The system of claim 13, wherein the position sensor comprises an arm and displacement of the arm by the flag generates an electrical signal associated with the actual position of the piston.

18. The system of claim 13, wherein the skin treatment solution is spray tanning solution.

* * * * *